Figure 1:
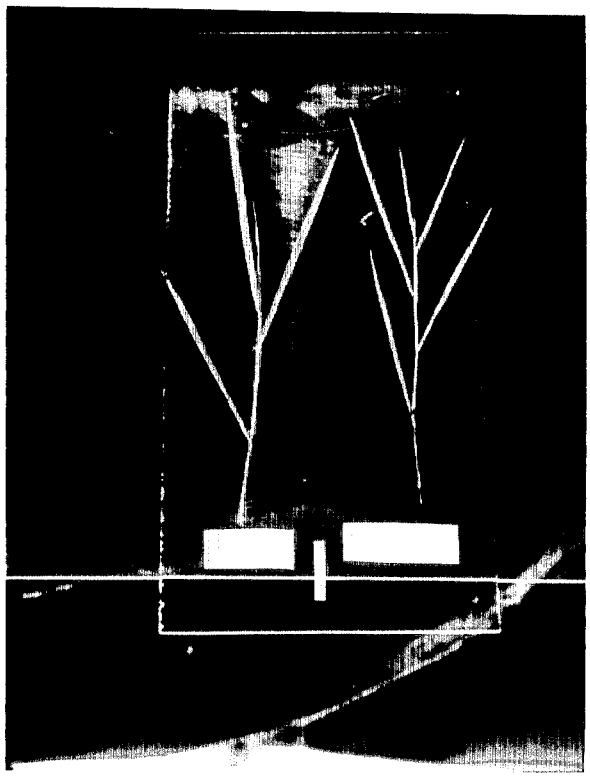

United States Patent [19]

Whiting

[11] Patent Number: Plant 5,465

[45] Date of Patent: May 7, 1985

[54] *DIGITARIA DIDACTYLA* GRASS PLANT

[75] Inventor: Hubert F. Whiting, Fallbrook, Calif.

[73] Assignee: Amfac Garden Perry's Inc., Ventura, Calif.

[21] Appl. No.: 539,742

[22] Filed: Oct. 6, 1983

[51] Int. Cl.[3] ..... A01H 5/00

[52] U.S. Cl. ..... Plt./88

[58] Field of Search ..... Plt./88

*Primary Examiner*—Robert E. Bagwill

[57] ABSTRACT

I disclose that my herein invention of a new variety of *Digitaria Didactyla* grass plant was discovered by me through my cross-pollinating selected varieties of *Digitaria Didactyla* grass plant then through asexual repropagation selected the new and distinct variety of *Digitaria Didactyla* grass plant which produces an excellent turfgrass of fine texture with very little thatch buildup, the color of the grass is a moderate green color as defined in the ISCC-NBS Centroid color chart; the stigmas of the new variety of *Digitaria Didactyla* grass plant are very dark purplish red color as defined in the ISCC-NBS Centroid color chart; the anthers of the new variety of *Digitaria Didactyla* grass plant are grayish reddish purple color as defined in the ISCC-NBS Centroid color chart; the new variety of *Digitaria Didactyla* grass plant is glabrous except for a few hairs around the stolon and culm nodes and has a more dense texture.

4 Drawing Figures

The present invention and discovery relates to a new and distinct variety of *Digitaria didactyla* grass plant which was discovered by me through cross-pollination of collected varieties of *Digitaria didactyla* grass plants. This cross-pollination was done by me at Indio, Calif., about 34 degrees north latitude. I harvested seeds from this cross-pollination of the selected varieties of *Digitaria didactyla* grass plants and planted these seeds out in germinating trays. Shortly after the seeds germinated, I transplanted each separate seedling into one gallon containers. There were 331 of these seedlings planted out by me in this way. As these seedlings grew and matured, I selected the most desirable for turfgrass potential. This left 105 seedlings. These 105 seedlings were then each individually broken up by me into small pieces of stolons, then I planted these small pieces of stolons into the soil in an area that was three feet square. When this process was completed, I had 105 individual seedlings planted in 105 three foot square plots, all asexually transplanted by me. The location of this transplanting was at Fallbrook, Calif. Once these 105 three foot square plots became established through the spreading of the planted stolons, I formed a turfgrass surface through regular mowing. I again made selections from the 105 plots. The selections I made this time were again individually transplanted by me asexually by breaking sufficient stolon material of each separate selection to further replant the now 23 selections into larger individual separate plots of ten feet by eight feet. Once these larger plots became established through the spreading of the planted stolons I formed a turfgrass surface through regular mowing. I again made selections from these 23 plots. The new claimed variety of *Digitaria didactyla* grass plant is one of those selections, and its designation is D-20. This new selected variety of *Digitaria didactyla* grass plant spread by stolons to produce an excellent turfgrass surface when regularly mown. I then asexually transplanted this new claimed variety of *Digitaria didactyla* grass plant into replicated randomized plots and, after complete establishment and regular mowing, I observed that this new claimed variety of *Digitaria didactyla* grass plant retained a green color longer into the winter periods after a very short time loss of some of its green color, and then regained complete green color. This green color retention ability was superior to the closest known variety of *Digitaria didactyla* grass plant. This new claimed variety of *Digitaria didactyla* produced a finer textured surface with less thatch build-up than the closest known variety of *Digitaria didactyla* grass plant. During the continued asexual reproduction by stolons, I have confirmed that the above-described characteristics are transmitted through succeeding propagations, and have confirmed that the new variety of *Digitaria didactyla* grass plant has the following unique combination of characteristics. The new and distinct variety of *Digitaria didactyla* grass plant is illustrated in the accompanying color photographs, with photographs of the closest known *Digitaria didactyla* grass plant. The most noticeable variations between the claimed variety of *Digitaria didactyla* grass plant and the closest known variety is that the claimed variety is a lighter green color of a finer, more dense texture with stigmas very dark, purplish red color and anthers of grayish reddish purple color. The new claimed variety of *Digitaria didactyla* grass plant is glabrous except for a few hairs around the stolon and culm nodes.

IN THE DRAWINGS

FIG. 1 is a photograph of two culms taken from the same test area, one piece is of the new and distinct variety of *Digitaria didactyla* grass plant, the other piece of culm is of the closest-known variety of *Digitaria didactyla* grass plant (identified by prior art). This photograph shows the new claimed variety of finer leaf blades.

Figure 2:
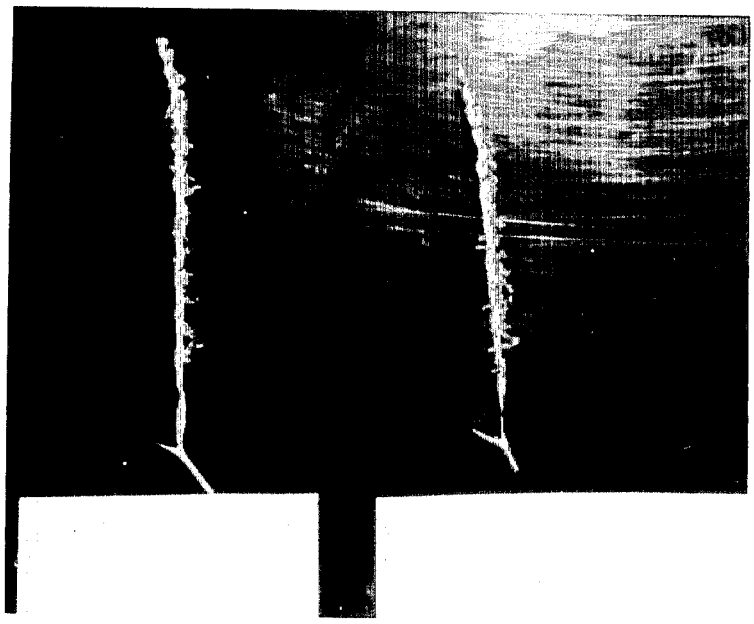

FIG. 2 is a photograph of spikes taken from the same test area of the new claimed variety of *Digitaria didactyla* grass plant, and the closest-known variety of *Digitaria didactyla* grass plant (identified by prior art). This photograph shows the very dark, purplish red colored stigmas, Color Number 260.v.d.pr. of the ISCC-NBS Centroid color chart, of the new claimed variety of *Digitaria didactyla* grass plant, compared to the closest-known variety of *Digitaria didactyla* grass plant, which has strong reddish purple colored stigmas, Color Number 237.s.rp. of the ISCC-NBS Centroid color chart.

Figure 3:
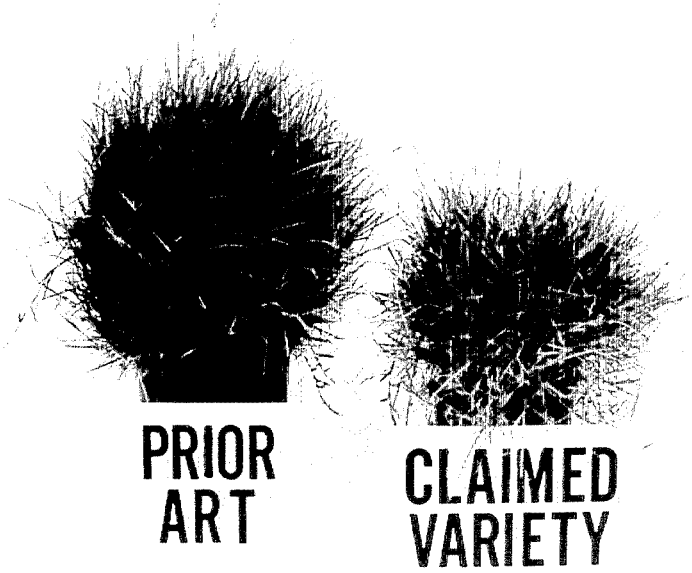

FIG. 3 is a photograph showing side views of pots containing the new and distinct variety of *Digitaria didactyla* grass plant and the closest-known variety of *Digitaria didactyla* grass plant (identified by prior art), both grasses being taken from the same test area and potted at the same time and further showing both grasses being unmown or uncut. This photograph shows the moderate green color, Color Number 145.m.g. of the ISCC-NBS Centroid color chart of the new claimed variety of *Digitaria didactyla* grass plant, compared to the closest-know variety of *Digitaria didactyla* grass plant, which is a moderate bluish-green color, Color Number 164.m.bg. of the ISCC-NBS Centroid color chart.

Figure 4:
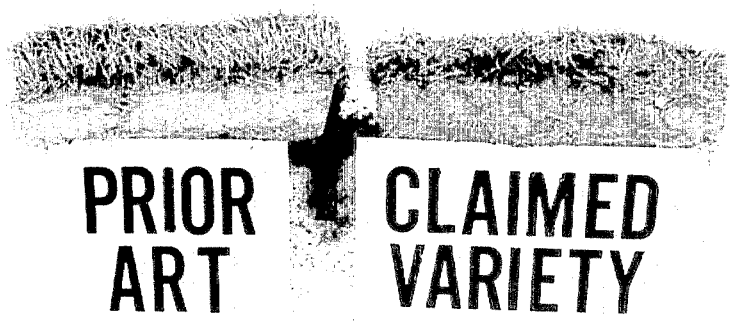

FIG. 4 is a photograph showing side views of sod pieces taken from the same test area of the new claimed variety of *Digitaria didactyla* grass plant and the closest-known variety of *Digitaria didactyla* grass plant (identified by prior art), which sod pieces have been subject to the same mowing conditions at virtually the same time with identical maintenance practices. This photograph shows the lack of thatch of the new claimed variety of *Digitaria didactyla* grass plant, compared to the closest-known variety of *Digitaria didactyla* grass plant (identified by prior art), which has more thatch build-up.

A detailed description of the new distinct variety of *Digitaria didactyla* grass plant is:

(a) An attractive, moderate green color, Color Number145.m.g. of the ISCC-NBS Centroid color chart.

(b) The grass is low-growing, erect in habit.

(c) The grass spreads by stolons and rhizomes, forming a dense, uniform surface with an extensive root system.

(d) Culms vary in height from 6–27 centimeters.

(e) Leaves rolled in bud shoot.

(f) The blade is V-shaped in cross-section, keeled and gradually tapering to an acute point.

(g) The first mature leaf is 2.5–3 millimeters in width and 25–70 millimeters in length.

(h) The leaf blade is glabrous, except at the base of the leaf close to the ligule, where a few hairs are present.

(i) The ligule is membranous acute and medium in height.

(j) Auricles are absent.

(k) The collar is narrow.

(l) The sheath is glabrous, split with margins overlapping.

(m) The entire plant is glabrous, except on the upper leaf surface, near the ligule on top of the sheath around the internodes.

(n) The internodal spaces on the stolons are 1–4 centimeters and on the culms, 1–5 centimeters.

(o) Inflorescence consists of 2–3 spikes at the top of the main stem, deflexed at maturity from 25–45 millimeters long.

(p) The spikelets are glabrous in two rows 2–3 millimeters long, blunt at their base, pointed at their tips, borne singly on short branches and glumes are present; the spikelet contains stigmas of very dark, purplish red, Color Number 260.v.d.pr. of the ISCC-NBS Centroid color chart, and anthers of grayish reddish purple, Color Number 245.gy.rp. of the ISCC-NBS Centroid color chart.

A detailed description of the closest known variety of the species of *Digitaria didactyla* grass plant is:

By comparison, the closest known variety of the species is described and claimed in my plant patent application, Ser. No. 432,977, filed Dec. 15, 1982, cultivar designation D-40 on a *Digitaria didactyla* Grass Plant. Reference to the "other *Digitaria didactyla*" grass in the above description refers to the grass plant described in my application, Ser. No. 432,977.

By comparison, the closest known variety of the species (application Ser. No. 432,977) is:

(a) An attractive, moderate bluish-green color, Color Number 164.m.bg. of the Centroid color chart.

(b) The grass is low-growing, erect in habit.

(c) The grass spreads by stolons and rhizomes, forming a dense, uniform surface with an extensive root system.

(d) Culms vary in height from 8 to 35 centimeters.

(e) Leaves rolled in bud shoot.

(f) The blade is V-shaped in cross-section, keeled and gradually tapering to an acute point.

(g) The first mature leaf is 3–3.5 millimeters in width and 25–80 millimeters in length.

(h) The leaf blade is glabrous, except at the base of the leaf close to the ligule, where 3 to 4 hairs are present.

(i) The ligule is membranous acute and medium in height.

(j) Auricles are absent.

(k) The collar is narrow.

(l) The sheath is glabrous, split with margins overlapping.

(m) The entire plant is glabrous, except on the upper leaf surface near the ligule and on top of the sheath around the internodes.

(n) The internodal spaces on the stolons are 1–5 centimeters and on the culms, 1–6 centimeters.

(o) Inflorescence consists of 2–3 spikes at the top of the main stem, deflexed at maturity from 25–45 millimeters long.

(p) The spikelets are glabrous in two rows 2–3 millimeters long, blunt at their base, pointed at their tips, borne singly on short branches and glumes are present. The spikelet contains stigmas of strong, reddish-purple, Color Number 237.s.rp. of the ISCC-NBS Centroid color chart, and the anthers of dark purple, Color Number 224.d.p. of the ISCC-NBS Centroid color chart.

Having now described the new and distinct variety of *Digitaria didactyla* grass plant which I have discovered and asexually reproduced, I claim:

1. A new variety of *Digitaria didactyla* grass plant herein shown and described by a moderate green color as defined by the ISCC-NBS Centroid color chart; this new variety retains a superior greener color during the winter period by only losing some of its green color, and produces a finer more dense textured surface with a very small amount of thatch buildup; the anthers are a grayish reddish purple as defined by the ISCC-NBS Centroid color chart; the stigmas are of a very dark purplish red as defined by the ISCC-NBS Centroid color chart.

* * * * *